United States Patent [19]

Harbour et al.

[11] Patent Number: 5,631,227
[45] Date of Patent: May 20, 1997

[54] SOMATOTROPIN ANALOGS

[75] Inventors: Gary C. Harbour; John G. Hoogerheide, both of Kalamazoo; Robert L. Garlick, Augusta; Stephen B. Lyle; John E. Mott, both of Kalamazoo, all of Mich.

[73] Assignee: The Upjohn Company, Kalamazoo, Mich.

[21] Appl. No.: 462,255

[22] Filed: Jun. 5, 1995

Related U.S. Application Data

[63] Continuation of Ser. No. 365,999, Dec. 29, 1994, abandoned, which is a continuation of Ser. No. 171,874, Dec. 22, 1993, abandoned, which is a continuation of Ser. No. 929,796, Aug. 13, 1992, abandoned, which is a continuation-in-part of Ser. No. 691,008, Jun. 18, 1991, abandoned, which is a continuation-in-part of Ser. No. 622,125, Dec. 3, 1990, abandoned, which is a continuation of Ser. No. 52,651, May 18, 1987, abandoned, which is a continuation of Ser. No. 891,726, Jul. 29, 1986, abandoned, which is a continuation-in-part of Ser. No. 777,154, Sep. 18, 1985, abandoned, said Ser. No. 691,008, Jun. 18, 1991, abandoned, is a continuation of Ser. No. 299,107, Jan. 19, 1989, abandoned.

[51] Int. Cl.[6] ............................ C07K 14/61; A61K 38/27
[52] U.S. Cl. ........................................... 514/12; 530/399
[58] Field of Search ............................. 514/12; 530/399

[56] References Cited

U.S. PATENT DOCUMENTS

| 4,521,409 | 6/1985 | Bauman | 514/21 |
| 5,089,473 | 2/1992 | Kriri et al. | 514/12 |
| 5,130,422 | 7/1992 | Kriri et al. | 514/12 |

FOREIGN PATENT DOCUMENTS

| 0047600 | 3/1982 | European Pat. Off. . |
| 0075444 | 8/1983 | European Pat. Off. . |
| 0085036 | 8/1983 | European Pat. Off. . |
| 0089666 | 9/1983 | European Pat. Off. . |
| 0103395 | 3/1984 | European Pat. Off. . |
| 0131843 | 1/1985 | European Pat. Off. . |
| WO87/01708 | 3/1987 | WIPO . |

OTHER PUBLICATIONS

Lewis et al., *Biochem. Biophys. Acta*, 214, 498–508, 1970.
Biochemistry 27: 4541–4546 (1988), Brems.
Abdel–Meguid et al., *Proc. Natl. Acad. Sci.*, 84, 6434–6437, 1987.
West et al., *Textbook of Biochemistry*, 4th ed., The Collier-Macmillan Co. N.Y. 1966, p. 1467.
Lewis et al., Biochem. Biophys. Acta, 214 pp. 498–508 (1970).
West et al, *Textbook of Biochemistry*, 45th ed., The Collier-MacMillan Co., NY, 1966 p. 1467.
Takano et al., *Chem Abst.*, 99, 107, Abst. #64639s.
Paladini, A.C., et al., Molecular Biology of Growth Hormone, CRC Critical Reviews in Biochem., 15:25–56 (1983).
Hart, I.C., et al., The Hetergeneity of Bovine Growth Hormone, Biochem. J., 218–573–581 (1984).
Wallis, M., et al., A Chromatographic Preparation of Ox Growth Hormone, Biochem., J., 100:593–600 (1966).
Lewis, U.J., et al., Kinetic Study of the Deamidation of Growth Hormone and Prolactin, Biochim, Biophys. Acta, 214:498–508 (1970).
Nucleic Acid Res. 10(20):6487 (1982).
Winter, G. and Fersht, A.R., TIBS, 2 p. 115 (1984).
Chou, P.Y. and Fasman, G.D., Ann. Rev. Biochem., 47, pp. 251–276 (1978).
Chou, P.Y. and Fasman, G.D., J. Mol. Biol., 115, pp. 135–175 (1977).

*Primary Examiner*—Howard E. Schain
*Attorney, Agent, or Firm*—James D. Darnley, Jr.; Paul J. Koivuniemi; Gregory W. Steele

[57] ABSTRACT

The present invention provides analogs of somatotropins wherein the asparagine residue corresponding to position 99 of a bovine somatotropin is replaced with a compound selected from the group consisting of proline, aspartic acid, glutamic acid, serine, glycine, serine-serine or serine-aspartic acid. Particularly preferred analogs are bovine somatotropin and their use to increase milk production.

11 Claims, No Drawings

SOMATOTROPIN ANALOGS

CROSS REFERENCE TO RELATED APPLICATIONS

This application is a continuation of U.S. patent application Ser. No. 08/365,999, filed 29 Dec. 1994; now abandoned which is a continuation of U.S. patent application Ser. No. 08/171,874, filed 22 Dec. 1993; now abandoned which is a continuation of U.S. patent application Ser. No. 07/929,796, filed 13 Aug. 1992; now abandoned which is a continuation-in-part of U.S. patent application Ser. No. 07/691,008, filed 18 Jun. 1991, now abandoned; which is a continuation-in-part of U.S. patent application Ser. No. 07/622,125, filed 3 Dec. 1990, now abandoned which is a continuation of U.S. patent application Ser. No. 07/052,651, filed 18 May 1987, now abandoned; which is a continuation of PCT Application No. PCT/US86/01860, filed 15 Sep. 1986; which is a continuation of U.S. patent application Ser. No. 06/891,726, filed 29 Jul. 1986, now abandoned; which is a continuation-in-part of U.S. patent application Ser. No. 06/777,154, filed 18 Sep. 1985 now abandoned U.S. patent application Ser. No. 07/691,008, represents the National phase of PCT/US89/05447, filed 11 Dec. 1989, which is a continuation of U.S. patent application Ser. No. 07/299,107, filed 19 Jan. 1987, now abandoned.

FIELD OF THE INVENTION

This invention discloses analogs of somatotropins originally having an asparagine located between residues 96–100. These analogs display increased bioactivity or increased stability or both as compared to their native species. More specifically, the invention relates to bovine or porcine somatotropin analogs, particularly with changes in amino acid residue 99.

BACKGROUND OF THE INVENTION

Bovine Somatotropin (BSt) is a growth hormone that has been well studied and the literature has been recently reviewed by Paladini, A. C. et al., CRC Crit. Rev. Biochem., 15:25–56 (1983). Somatotropins were originally discovered in pituitary gland extracts from various animal species. In general, somatotropins are conserved molecules and similarities in amino acid sequences and structure are found between animals of disparate evolutionary ranking.

Growth hormones including bovine growth hormone are globular proteins comprised of a single chain of approximately 200 amino acids, having 2–3 intramolecular disulfide bonds. Specifically, BSt has a single chain of 190–191 amino acids, a globular structure with two intramolecular disulfide bonds, and a molecular weight of approximately 22,000 daltons.

BSt extracted from pituitary glands is heterogeneous. At least six major forms of the protein have been described. The longest form has 191 amino acid residues and an ala-phe amino terminus. The second form has 190 amino acid residues and a phe amino terminus. The third form has 187 amino acid residues and a met amino terminus. The remaining three forms of BSt substitute valine for leucine at position 127. In addition to this heterogeneity, undefined heterogeneity of bovine somatotropin has also been described (Hart, I. C. et al., Biochem. J., 218:573–581 (1984); Wallace, M. and Dickson, H. B. F., Biochem. J., 100:593–600 (1965)).

Undefined electrophoretic heterogeneity is seen when the native extracts are fractionated by anion exchange chromatography. It has not been shown that the defined forms have different relative potency in bioassays. However, it has been shown that the undefined species of BSt when fractionated on ion exchange columns demonstrate varying degrees of bioactivity in rat growth models (Hart, et al. and Wallace and Dickson, supra.).

It is not known whether undefined heterogeneity exhibiting biological variation is due to genetic variability, to in vivo post-translational modification, to differences in phosphorylation (Liberti, J. P. et al., Biochem. and Biophys. Res. Comm., 128:713–720, (1985)), or to artifacts of isolation.

BSt either produced by recombinant microorganisms or extracted from pituitary gland tissue is estimated to be of great commercial value. It has the ability to increase lactation in dairy cattle and has the ability to increase size and meat production in beef cattle. Administration to cattle is a problem. It is estimated that upwards to 100 mg per animal per day or more will be needed to effect commercially acceptable improvements in production. Such a dosage will require efficient methods of administration. Improvements in the potency and stability of BSt such as described in this invention will be of benefit because of resulting reductions in the amount of drug administered to each animal per day.

Furthermore, one of the problems in preparing recombinantly-produced BSt (rBSt) is that liquid processing and storage of rBSt at acid or alkaline pH results in the conversion of the asparagine residue at position 99 to isoaspartic acid. The resulting rBSt is referred to as "early eluting rBSt" because it elutes earlier than native rBSt on reversed phase HPLC. Isoaspartate is formed when the asparagine side chain condenses with the peptide backbone resulting in the elimination of ammonia. Chain cleavage also occurs by a condensation reaction between the peptide backbone and the asparagine residue at position 99 of the rBSt molecule upon storage. The chain-cleaved product is covalently held together by the disulfide bond between cysteine residues 53 and 164 and has been called "early-early eluting rBSt" because of its eluting position relative to native and early eluting rBSt.

Because the instability that occurs due to the modification of asparagine 99 leads to a loss of native rBSt during its isolation, formulation and storage as reconstituted product, it would be advantageous to make an amino acid substitution at position 99 to produce an rBSt analog that is more stable while retaining or enhancing its biological activity.

INFORMATION DISCLOSURE

Analogs of BSt are known (see, for example, European patent applications 75,444 and 103,395 and Nucleic Acid Res., 10(20):6487 (1982)).

G. Winter and A. R. Fersht, TIBS, 2, p. 115 (1984) review the alteration of enzyme activity by changing amino acid composition at key sequence locations.

P. Y. Chou and G. D. Fasman, Ann. Rev. Biochem., 47, pp. 251–76 (1978) refer to the use of amino acid sequences to predict the secondary and tertiary structure of proteins.

P. Y. Chou and G. D. Fasman, J. Mol. Biol., 115:135–75 (1977) refer to β-turns in proteins. From analysis of 459 β-turn regions in 29 proteins of known sequence and X-ray structure, they found that the most frequently occurring amino acids in the third position of a β-turn are asparagine, aspartic acid, and glycine. The residues with the highest β-turn potential in all positions within the turn are proline, glycine, asparagine, aspartic acid, and serine.

BRIEF DESCRIPTION OF THE TABLES

Table A is the amino acid sequence of bovine somatotropin with the relevant asparagine within the specific β-turn of interest, i.e., position 99, underlined.

Table B is the original nucleic acid sequence of bovine somatotropin with the relevant codon within the β-turn of interest underlined. The chart also shows two of the synthetic oligonucleotides used in embodiments of the invention.

Table 1 shows the construction of plasmid pUC19(d).

Table 2 shows the construction of plasmid pUC19(d)-bSt from plasmids pBGH 33-4 and pUC19(d).

Table 3 shows the construction of plasmid pM13-BSt' from plasmids pBGH 33-4 and M13 mp-19 RF.

Table 4 shows the construction of plasmid pUC19(d)-bSt* encoding aspartic acid at position 98.

Table 5 shows the construction of plasmid pBGH33-4-"Glu98" encoding glutamic acid at position 98.

Table 6 shows the construction of plasmid pUC8-bSt' from plasmids pBGH33-4 and pUC-8.

Table 7 shows the construction of plasmid pUC-bSt' ala from plasmids pUC8-bSt' and a 5' synthetic oligonucleotide.

Table 8 shows the construction of plasmid pUC19(d)bSt-ala from plasmids pUC19(d)bSt and pUC8-bSt'ala.

Table 9 shows the oligonucleotides used in constructing rBSt analogs of the invention.

Table 10 is the cloning of the BSt gene M4-99ser into a pURA vector.

SUMMARY OF THE INVENTION

This invention relates to the enhancement of bioactivity or stability in liquid storage, or both, of animal somatotropins and analogs thereof, in particular BSt, by substituting different amino acids for the asparagine corresponding to the residues at positions 96–101 relative to native BSt. Similar changes can be made in somatotropins from other animals, particularly mammals, including porcine, fish, ovine, horse, rat, monkey, and human.

More specifically, and preferred, are those species of BSt-like compounds wherein the asparagine located at amino acid residue 99 is replaced with a different amino acid residue including specifically glycine, serine, proline, aspartic acid, glutamic acid, serine-serine or serine-aspartic acid.

More specifically, the animal somatotropin is selected from the group consisting of bovine, porcine, fish, ovine, horse, rat, monkey, and human somatotropins.

Even more specifically, the animal somatotropin is bovine somatotropin.

Also provided is a method for enhancing the growth of an animal, particularly a mammal, and more particularly a bovine, which comprises administering to the animal an effective amount of a somatotropin of the instant invention, and, in particular, where the animal is a bovine and the somatotropin is BSt.

Also provided is a method for increasing milk production in a female ruminant comprising administering to the female ruminant an effective amount of an animal somatotropin of the instant invention, and, in particular, where the animal is a bovine and the somatotropin is BSt.

Although not all mammalian somatotropins contain asparagine at the appropriate location, porcine and human growth hormones in addition to BSt do contain a single asparagine at the residues 96–101 of their amino acid sequence. Accordingly, all native mammalian somatotropins having an asparagine at this region, which corresponds to β-turn, are embraced by this invention. In addition to the native species, analogs of BSt and other mammalian somatotropins having an asparagine within the 96–101 residues are embraced by this invention. Analogs include somatotropin-like compounds which embrace all proteins having sufficient similarity in amino acid sequence to elicit a growth response in the hypophysectomized rat assay or in the mammal from which it is derived.

DETAILED DESCRIPTION

The mammalian somatotropins are very similar in amino acid sequence and physical structure. Although the processes described below are directed towards the modification of BSt, the processes are equally applicable to any mammalian somatotropin having the requisite asparagine residue available for substitution.

Due to the polymorphism of somatotropins, the position numbers of amino acid residues of the various somatotropins may differ. The term "native mammalian somatotropin" embraces these naturally occurring species. Chart 1 illustrates the specific region of one species of BSt that corresponds to the position 99 residue modified by this invention. The numbering for other somatotropins may differ where other species or analogs are involved and, therefore, it is helpful to note that the asparagine of interest appears within a β-turn which is determined according to Chow and Fasman, J. Mol. Biol., 115:135 (1977) and Ann. Rev. Biochem., 47:251 (1978). Using the general region enumerated as 96–101 of the native sequences, the knowledge that the region is a β-turn, and the location of asparagine 99 in Chart 1, those of ordinary skill in the art can readily locate corresponding amino acids in other mammalian somatotropins, or their analogs, to achieve the desired liquid storage stability, enhanced bioactivity, and/or uniform potency as exemplified by the instant invention.

Both chemical and genetic modifications of this region are embraced by this invention. The preferred chemical deamidation of BSt is with alkaline treatment. The preferred genetic modification involves single site specific mutation methods for insertion of various amino acids in replacement of the naturally occurring asparagine. Chemical deamidation results in both aspartic acid and isoaspartate being formed in place of the naturally occurring asparagine.

The phrase "animal somatotropin" refers to somatotropins originating from animals, e.g., mammals, and includes somatotropins derived from either natural sources, e.g., pituitary gland tissue or from microorganisms transformed by recombinant genetics to produce a naturally-occurring form of somatotropin. When a specific mammalian source is named such as a bovine somatotropin or a somatotropin of bovine origin, the somatotropin includes those derived from either natural sources or from transformed microorganisms.

The term "microorganism" is used herein to include both single cellular prokaryotic and eukaryotic organisms such as bacteria, yeast, actinomycetes and single cells from higher plants and animals grown in cell culture.

The term "native" refers to naturally-occurring forms of somatotropins which may have been derived from either natural sources, e.g., pituitary gland tissue or from microorganisms transformed by recombinant genetics to produce a somatotropin having the same amino acid sequence as the naturally-occurring form of somatotropin.

The mammalian somatotropins are very similar in amino acid sequence and physical structure. Although the processes described in the Examples are directed toward BSt, the processes are equally applicable to any animal, e.g., mammalian, somatotropin having the requisite asparagine residue available for replacement particularly wherein similar liquid processing and storage problems are encountered.

The phrase "closest-related native somatotropin" refers to the naturally-occurring form of mammalian somatotropin which when compared to a specific somatotropin-like protein is more closely identical in amino acid sequence than any other naturally-occurring form of mammalian somatotropin.

The phrase "somatotropin-like protein" refers to both native forms of somatotropins and to analogs of native somatotropins provided that the analogs have sufficient protein identity with their parent compounds to demonstrate bioactivity as either a growth promoter or as a stimulant for milk production.

The term "vector" includes both cloning plasmids and plasmids which are capable of directing the expression of a somatotropin by virtue of the cDNA encoding the somatotropin being operatively linked to a promoter capable of being recognized by a microorganism.

The high relative potency of the BSt analogs of the present invention is readily determined using hypophysectomized rats. Evans, H. M. and Long J. A., Anat. Rec., 21:61 (1921). Relative increases in total body weight are recorded using pituitary BSt and various BSt analogs of the invention.

Administration into dairy cattle is according to known methods using any route effective to deliver the required dosage to the animal's circulatory system. Modes of administration include intramuscular injections, subcutaneous injections and the use of timed-release implants and formulations. The preferred mode of administration is by subcutaneous injection using a timed-release formulation. Appropriate vehicles for injections include physiologically compatible buffers such as sodium bicarbonate, sodium phosphate, or ammonium phosphate solutions. Timed-release implants, e.g., U.S. Pat. No. 4,333,919, are known in the art.

The effective dosage range is from 1.0 to 200 milligrams per animal per day. The greater the amount of BSt given, the greater the resulting increase in growth, lactation or numbers of mammary parenchymal cells. Most preferably, the dosage range would be from 10 to 50 milligrams per day.

Mammalian growth hormones are very similar in their amino acid sequences and hormones originating from one animal source can enhance the growth of other unrelated species of animals. For purposes of increasing growth rate of animals, BSt analogs can be used to produce increased growth in the same animal species in which native BSt has been shown to have growth-related bioactivity such as bovines, sheep, rats, salmon and chickens. The preferred animals are bovine used for beef cattle such as bulls, heifers or steers.

Beef cattle are slaughtered just prior to reaching full maturity and size. The BSt analogs of the invention can be used to produce increased growth rates in beef cattle by administration any time between weaning until slaughter. The analogs may be administered to beef cattle for a minimum of 30 days and for a maximum of 450 days depending upon desired time of slaughter. Animals used for veal are typically slaughtered at approximately 6 months of age and 10 to 30 mg/day of a BSt analog of the invention is administered up until the age of slaughter to effectuate desired increases in growth rate.

For purposes of increasing lactation in bovines, particularly dairy cows, the BSt of the invention are administered between 30 and 90 days postpartum and continued for up to 300 days. The BSt analogs will also increase lactation in other commercial milk-producing animals such as goats or sheep.

Methods are known in the art for increasing the number of mammary parenchymal cells in female ruminants, particularly dairy heifers, see e.g., U.S. Pat. No. 4,521,409, which is incorporated by reference. Briefly, the ruminants (dairy heifers, sheep and goats, among others) are treated with the BSt analogs of the invention sometime around the onset of puberty. Treatment is continued until first conception or parturition. More particularly, administration of the analogs in dairy heifers can be begun within 30 days of the expected onset of puberty and continued up until 100 days after the onset of puberty. Puberty is defined by the period beginning with the initiation of the sexual process and lasting up until the maturation of the sexual organs. The precise time of administration will depend upon the particular breed of animal, its nutritional status and management practices.

Throughout the specification and claims, parameters described by a range such as 1 to 5 or 1–5 milligrams, days, hours, degrees, or pH units are meant to be inclusive unless stated otherwise.

Site-Directed Mutagenesis: Several techniques for site-directed mutagenesis have been developed for introducing specific changes in a DNA sequence and may be used to produce the compounds of the instant invention (Kramer, W., et al., Nucl. Acids Res., 12:9441–56 (1984); Mandecki, W., Proc. Natl. Acad. Sci. USA, 83:7177–81 (1986); Zoller, M. J. and Smith, M., Nucl. Acids Res., 10:6487–6500 (1982); Norrander, J., et al., Gene, 26:101–106 (1983); Kunkel, T. A., Proc. Natl. Acad. Sci. USA, 82:488–92 (1985); Schold, A., et. al., DNA, 3:469–77 (1984)). We employed the primer directed mutagenesis technique of Schold et al. for five of the seven analogs produced, except that only one primer is used for the initial hybridization reaction and 18 µl of $T_4$ gene 32 protein is added to the extension reaction.

Colony Filter Hybridization: The screening technique of filter hybridization is based upon the ability of a single-stranded segment of DNA to locate its complementary sequence and hybridize to form a double-stranded segment, Hanahan, D. and Meselson, M., Meth. Enzymol., 100:33342 (1983). The thermal stability of this binding is dependent upon the number of matches and mismatches contained within the double stranded region. The more mismatches it contains, the weaker the base-pair binding and the lower the temperature necessary to disrupt the DNA binding. This temperature differential is exploited during colony filter hybridization, Bryan, R. N., et. al., Diagnosis of Clinical Samples with Synthetic Oligonucleotide Hybridization Probes, Microbiology (1986) pp 113–116*. By constructing a mutant oligomer which maximizes the temperature differential between the native and mutant sequence, it is possible to hybridize at a lower temperature allowing binding of the probe to matched and nearly matched sequences. Upon washing at elevated temperatures, the mismatched probe-DNA duplex becomes unstable and disassociates while the perfectly matched duplex remains bound. The matched duplex will then produce the darkest signal on an autoradiogram thus forming a detection method for a colony containing the desired sequence. DNA from this colony can then be isolated and sequenced.

For filter preparation, nitrocellulose filters are overlayed onto plates and wetted. The filters and plates are marked for orientation and the filters are then carefully lifted off the plates. The master filter plates are incubated overnight at room temperature to allow regrowth of the colonies. The filters are denatured by laying them one by one onto Whatman paper, soaked in 0.5M sodium hydroxide, 1.5M sodium chloride for 10 minutes and neutralized in two successive changes of Whatman paper soaked in 1M Tris, pH 7.4, 1.5M sodium chloride, for 10 minutes each and air dried on fresh Whatman paper for 30 minutes. They are then baked for 2 hours at 80° C. in vacuum.

The kinase reaction to radiolabel the mutant oligonucleotide for use as a probe is as follows: 2 µg of oligo, 2 µl of 10X kinase buffer, 100 µCi τ32-P ATP, 2 µl T4 kinase and 4

μl water are mixed and incubated for 1 hour at 37° C. A 1 ml column is packed with DEAE-Sephacel in a 10 ml disposable column and equilibrated with 2–3 ml of high salt buffer (1.5M sodium chloride in TE) and then 2–3 ml of low salt buffer (0.2M sodium chloride in TE). The kinase reaction is diluted with 200 μl of low salt buffer and loaded directly into the column. The column is washed with 10 ml of low salt buffer until no further counts elute from the column. The probe is eluted in 4 ml of high salt buffer.

To hybridize, the filters are placed in a crystallization dish and batch pre-hybridized in 5X Denhardts (1% BSA, 1% Ficoll and 1% PVP), 5X SSC (0.75M sodium chloride, 0.075M sodium citrate) and 0.1% SDS for 1 hour at 40° C. The hybridization solution is changed and the probe is added. The dish is covered and the hybridization done overnight with gentle agitation. The filters are then rinsed with several changes of 5X SSC, 0.1% SDS. The filters sit in this solution while the water bath and wash solution (5X SSC, 0.1% SDS) is heated up to washing temperature (46° C.). The filters are transferred one by one to a fresh crystallization dish and washed 3×20 minutes, changing dishes after each wash. They are then air dried on Whatman paper, wrapped in Saran wrap and exposed as necessary.

Vector DNA Preparation: DNA for sequencing is obtained according to the method of L. Agelion and T. Chen, Gene Anal. Techn., 3:86–89 (1986) except that only one combined phenol/chloroform extraction is performed and the DNA is not spin-dialyzed through a Sephadex G-50 column.

Sequencing: Double-stranded sequencing is performed according to the following protocol: 3 μl 2N sodium hydroxide, 2 mM EDTA is added to 12 μl of DNA (2 μg) and incubated for 15 minutes. 6 μl 3M NaOAc, 1 μl primer and 100 μl 95% ethanol are added and the DNA precipitated on dry ice for 20–30 minutes. The pellet is collected, washed and vacuum dried. It is dissolved in 13 μl water and 4 μl RT buffer (0.3M Tris-HCl, pH 8.3, 0.375M sodium chloride, 37.5 mM magnesium chloride, 2.5 mM dithiothreatol), 2 μl τ32P dCTP and 1 μl reverse transcriptase are added. 4 μl of this mix is pipetted into 4 eppendorf tubes, each containing 1 μl of G mix, A mix, T mix or C mix. The tubes are incubated for 10 minutes at 42° C. 1 μl of chase mix (0.25 mM dNTPs) is added and they are incubated for an additional 5 minutes. 10 μl stop solution (80% formamide, 10 mM sodium chloride, 1 mM EDTA, 0.1% xylene cyanol and 0.1% bromphenol blue) is added, the reactions are boiled 3 minutes and 3 μl of each is loaded onto a sequencing gel.

Induction Protocol and SDS-PAGE Analysis: See PCT/US 88/00328.

Unless otherwise indicated, methodology presented below relating to procedures for carrying out recombinant genetic manipulations which include enzymatic reaction conditions, DNA isolation and purification, and culturing of transformed bacterial colonies are according to Maniatis et al., Molecular Cloning: A Laboratory Manual. Cold Spring Harbor Laboratory, (1982).

Conventions used to represent plasmids and fragments in Charts 1–10, though unique to this application, are meant to be synonymous with conventional representations of plasmids and their fragments. Unlike the conventional circular figures, the single line figures on the charts represent both circular and linear double-stranded DNA with initiation or transcription occurring from left to right (5' to 3') where indicated. Asterisks (*) represent the bridging of nucleotides to complete the circular form of the plasmids. Fragments do not have asterisk marks because they are linear pieces of double stranded DNA. Endonuclease restriction sites are indicated above the line. Gene markers are indicated below the line. The relative spacing between markers do not indicate actual distances but are only meant to indicate their relative positions on the illustrated DNA sequence.

EXAMPLES

Example 1

Recombinant BSt.

Recombinant BSt is known and can be produced by a number of published procedures such as described in Schoner, B. E., et al., PNAS, USA, 81:5403–5407 (1984); Seeburg, P. H., DNA, 2:3745 (1983) and European patent application 75,444. The choice of rBSt species is not relevant to this invention. N-terminal heterogeneity is known to exist for BSt. Two species exemplified herein are the amino-terminal ala-phe- and phe- forms of rBSt. The chemical deamidation and biological tests are exemplified with ala-phe rBSt. Forms of rBSt that are expressed by E. coli. may have a methionine residue in place at the N-terminal portion of the protein. This additional residue does not influence the nature of this invention and its presence is optional.

Example 2

Introduction of nucleotide changes at positions "98" and "99" in rBSt using recombinant genetics.

Changes in the DNA sequence of rBSt are made by site-directed mutagenesis using the methods of Zoller and Smith (Nucl. Acid Res., 10:6487–6500, (1982), and Methods in Enzymology, 100:468–500, (1983)). In brief, a segment of DNA from the rBSt gene is cloned into M13mp phage vectors and used to infect E. coli. Single stranded DNA can be isolated from the M13 phage virions, and hybridized with a synthetic oligomer which contains the desired base changes. A double stranded region is isolated after primer extension by digestion with restriction endonucleases and cloned into a "transition vector". Clones containing the transition vector are then sequenced to verify the desired change. The transition vector provides restriction sites which allow the reconstitution of the altered rBSt gene and its introduction into an expression vector.

Example 2A is based on the modified rBSt gene in the expression vector pBGH33-4, as described in European Patent application 75444 and Great Britain Patent No. 2,147,902B. This gene has been modified in its N-terminal DNA sequence to enhance expression of the rBSt protein. This example should not be construed as a limitation upon the disclosed invention. The use of pBGH33-4 to exemplify site specific mutations of rBSt at codon 98 is a matter of convenience. Alternative vectors containing equally useful cDNA encoding for BSt have been described. It should be noted that pBGH33-4 contains the phe-rBSt gene and amino acid references to position 98 correspond to position 99 in the ala-phe-rBSt used for chemical deamidation and biological testing.

Example 2B discloses a convenient method for inserting an alanine into the codon at position 1 of phe-rBSt cDNA.

Example 2A

The introduction of glutamic or aspartic acid at position "99" of phe-rBSt.

I. Construction of the transition vector

The purpose of the transition vector is to provide a vector which has manipulatable restriction sites for reconstruction of the intact rBSt gene after a sub-segment has been mutagenized. Specifically, this example takes advantage of a PstI restriction site in the rBSt cDNA sequence located upstream of the 98th codon. This PstI site is unique in the gene but is not unique for the vector pBGH33-4. To modify codon 98, a PstI/BamHI restriction fragment encompassing this sequence is cloned into the M13mp19 vector (Messing, Methods in Enzymology 101:20–78 (1983) and Yanisck-Perron et al., Gene 33:103–119 (1985)). These M13mp vectors are commercially available (International Biotechnology, Inc., New Haven, Conn., USA). After mutagenesis of the PstI/BamHI rBSt sub-segment, the rBSt gene is cloned into a transition vector in which the PstI and BamHI restriction sites of the original rBSt gene are unique.

The construction of pUC19(d)—Chart 1.

This vector has no PstI sites. The pUC19 vector (International Biotechnology, Inc.), contains a single PstI site located in a poly-linker (Yanisch-Perron et al., (1985) supra). The site lies between the HinII and HindIII restriction sites. The PstI site is deleted by cutting purified DNA at the HinII and HindIII sites, filling the 5' overhang of the HindIII site with PolI Klenow (PolIk), purifying the large cut vector fragment by agarose gel electrophoresis and electroelution, ligating with T4 DNA ligase and ATP, and transforming competent cells selecting for resistance to ampicillin. Verification of the presence of pUC19(d) in a clone is obtained by isolating DNA from several clones using the method of Birnboim and Doly (Nucl. Acid Res., 7:1513–1523 (1979)). The isolated DNA is then analyzed by restriction digestions for vectors which are not cut by HindII, HinII, or PstI and are cut once by XbaI and BamHI. These procedures are described in detail in Maniatis et al., Molecular Cloning: A Laboratory Manual, Cold Spring Harbor Laboratory (1982). The resultant vector is designated as pUC19(d).

The construction of pUC19(d)-BSt—Chart 2.

The entire rBSt gene is isolated from the vector pBGH33-4 on an XbaI, BamHI restriction fragment 1 (0.9 kb) and cloned into the complementary XbaI, BamHI restriction sites of pUC19(d). To insure efficient cloning, fragment 1 (0.9 kb) is isolated from pBGH33-4, and fragment 2 (2.7 kb) is isolated from pUC19(d) after the individual vectors are digested with XbaI and BamHI. The fragments are cut from a gel and isolated by electroelution. The steps involved are the same as those described for the construction of pUC19(d). The resultant vector is designated as pUC19(d)-BSt.

Construction of pM13-BSt'—Chart 3.

To obtain pM13-BSt', a sub-fragment of the rBSt gene encoding the asparagine residue at position 98, is cloned into the M13mp19 phage vector. The M13 vectors permit the isolation of single stranded closed circular DNA from phage virions isolated from infected bacteria. This single stranded DNA is then hybridized with synthetic oligomers that have been altered for codon 98 forming a limited heteroduplex.

A M13 clone containing pM13-BSt' is constructed by isolating the PstI/BamHI fragment 3 (0.7 kb) from the pBGH33-4 and cloning into the corresponding PstI/BamHI restriction sites of M13mp19 vector. The M13mp19 cloning protocol has been described by Messing, Methods in Enzymology, 101:20–78 (1983). In brief, RF (replicative form) DNA is isolated from M13Mp19 infected cells. The isolated DNA is subjected to restriction digestion by PstI and BamHI endonucleases. The large fragment (about 7.2 kb) is purified and ligated to fragment 3 to yield pM13-BSt'. E. coli. cells are transfected and individual plaques are isolated. The RF DNA is isolated again and the insertion of the fragment is confirmed by analytical digestions with restriction endonucleases. The PstI restriction site for rBSt cDNA corresponds to amino acids 89 and 90 of rBSt. The target codon, 98, is located within the PstI, BamHI fragment.

II. Modification of position 98

Design of DNA Oligomers.

Two synthetic oligonucleotides, 39 nucleotides in length are shown in CHART B. These oligonucleotides vary in their sequences for the codon coding for the native asparagine residue at position 98. The two oligomers will result in amino acid changes to either aspartic acid (asp), or glutamic acid (glu) at position 98. Nine nucleotides are present after the modification at position 98 to ensure the availability of 3' end which can be extended by any of several polymerases (i.e., AMV reverse transcriptase, T4 DNA polymerase or Pol I Klenow fragment). The oligomers are made using an Applied Biosystems nucleotide synthesizer.

Preparation of Single Stranded DNA.

Preparation of single strand DNA from the M13 infected E. coli. clones has been described by Messing (supra). The preferred E. coli. host is JM101 also described by Messing. This host has been modified by the introduction of a the dam-13::Tn9 by P1 transduction (Miller, Experiments in Molecular Genetics, Cold Spring Harbor Laboratory, (1972)) and selection for chloramphenicol resistance. An appropriate strain containing the dam-3 allele is publicly available from the E. coli. Genetic Stock Center, Yale University, New Haven, Conn. USA. The dam allele is used to prevent methylation of the single stranded DNA which in turn prevents preferred correction of the altered codon (Pukkila et al. Genetics 104:571–582., (1983)).

Hybridization.

Hybridization conditions are described by Zoller and Smith (Methods in Enzymology 100:468–500, (1983)). An oligomer with the desired codon change at position 98 is hybridized in a 20 to 30 molar excess to its complement with 1 mole of the single stranded DNA molecules by heating at 65° C. and allowing the mixture to cool to room temperature.

Primer Extension.

After hybridization, the 3' end of the oligomer is used as a primer for extension by DNA PolIk. The extension is performed in the presence of 20 μC (alpha-32P)dATP and 5 mM each of dCTP, dGTP, and dTTP. The mixture is incubated at room temperature for 10 minutes, after which an excess of non-radioactive dATP is added. This increases the size of the heteroduplex and extends the double stranded region of the molecules to include the BamHI restriction sequence, thus creating a cleavable BamHI restriction site.

Isolation and Cloning of the Heteroduplex into pUC19 (d)-BSt*—Chart 4.

Primer extended molecules are subjected to restriction digestions with PstI and BamHI. This will generate a heteroduplex of approximately 700 bp which can be visualized by autoradiography after the reaction mixture is run on a non-denaturing acrylamide gel with appropriate sizing markers (Maniatis et al., supra). The band is cut out as a gel slice and the fragment is eluted from the gel.

This DNA which contains the desired codon change in one DNA strand is then ligated into the PstI, BamHI restriction sites of the transition vector pUC19(d)-BSt. The pUC19(d)-BSt vector is digested with the PstI and BamHI restriction enzymes to yield fragment 6 (3.0 kb) which is purified by gel electrophoresis and electroelution. This removes the normal coding sequence at position 98. Fragment 6 is then ligated to the heteroduplex fragment and transformed into competent cells selecting for resistance to ampicillin. The isolation of the heteroduplex fragment eliminates the need for alkaline sucrose gradients in the Zoller and Smith (supra, 1983)) protocol and insures the formation of a double stranded covalently closed molecule.

Identification of the change at Position 98.

Individual transformed cells are twice streaked from individual colonies for purification of cloned DNA. One colony for every originally transformed cell is selected and vector DNA is prepared by the protocol of Birnboim and Doly (supra). The double stranded vector DNA is sequenced by the dideoxy method using a synthesized primer to the rBSt sequence 5' to the PstI site and position 98 (Sanger et al., Proc. Natl. Acad. Sci., USA 74:5463–5467 (1977); Zagursky et al., Gene Anal. Techn., 2:89–94 (1985)). The theoretical yield of vectors having the desired changes will be 50%.

III. Construction of Expression Vector pBGH33-4-nGlu98n—Chart 5.

The modified rBSt gene can now be recloned as an XbaI, BamHI fragment from the transition vector, pUC19(d)-BSt*, into the expression vector pBGH33-4. The transition vector is digested with the restriction enzymes XbaI and BamHI and fragment 7 (1.0 kb) is obtained. Fragment 7, which contains the entire coding sequence for rBSt, is isolated. The rBSt expression vector pBGH33-4 is digested with the same enzymes and the vector fragment 8 (4.0 kb) is isolated. The two fragments are ligated and transformed into competent cells. The pBGH33-4 vector fragment provides a ribosomal binding site and the tryptophan promoter for the expression of the modified rBSt gene. The modified rBSt gene expression in this vector is inducible by methods known in the art. Purification of rBSt from transformed microorganisms is also known in the art.

Example 2B

The introduction of glutamic or aspartic acid into position 99 of ala-phe-rBSt.

Following the procedures outlined in Example 2A, it is possible to genetically alter the asparagine at position 99 of a ala-phe- form of rBSt. To obtain the ala-phe- form one can insert a codon encoding alanine between the methionine and phenylalanine codon at the Ntermini of the rBSt cDNA of pBGH33-4. The following protocol describes changing the coding sequence of the rBSt gene described in EP 75444 to code for a met-ala-phe-pro rBSt protein molecule. This modification can be made either before or after the changes previously described for the codon at position "98" in the rBSt molecule.

General Strategy.

The plasmid pBGH33-4 contains an XbaI restriction site located between the ribosomal binding site and the ATG initiation condon of the rBSt gene. Approximately 72 nucleotide downstream of this site there is a PvuII restriction site. A synthetic double stranded oligomer can be inserted between these two restriction sites which contains the additional ala condon at the second amino acid position. However, the PvuII restriction site is not unique for the gene. This problem can be circumvented by constructing a vector containing only that portion of the rBSt gene which is to be modified and in which this PvuII site is unique. The front end of the gene is modified and an intact rBSt gene is reconstructed.

The construction of pUCS-BSt'—Chart 6.

Plasmid pUC8-BSt' is constructed by digesting the DNA of pBGH33-4 with EcoRI and PstI restriction endonucleases. Fragment 9 (550 bp) is cut from an agarose gel and electroeluted. This fragment contains the trp promoter, a ribosomal binding site and the front half of the rBSt gene. The pUC8 vector (commercially available from Bethesda Research Laboratories, Gaithersburg, Md., USA) is digested with EcoRI and PstI and the 2.7 kb vector fragment 10 is isolated. The two purified DNA molecules are ligated and transformed into competent E. coli. cells. Cells containing the vectors are selected by resistance to ampicillin. DNA is isolated from the individual colonies by the Birnboim and Doly protocol and the vector construction is confirmed by analytical restriction analysis. The resultant vector is designated pUCS-BSt'. The vector is unique for the XbaI and PvuII restriction sites in the fragment cloned from pBGH33-4.

The construction of pUCS-BSt'-ala—Chart 7.

Plasmid pUCS-BSt' is isolated and digested with XbaI and PvuII restriction endonucleases. Fragment 11 (2.7 kb) is isolated. This removes the sequence for the first 23 amino acids of rBSt.

The following synthetic oligomers are made:

5'-CTAGAATGGTCTTCCCAGCTATGTCTCTATCTG G T C T A T T C G C T A A C G C T G T T C T T CGTGCTCAGCATCTTCATCAG-3'

5'-CTGATGAAGATGCTGAGCACGAAGAACAGCG T T C G C G A A T A G A C C A G A T A G A G A C A TAGCTGGGAAGACCATT-3'

These two synthetic oligomers are hybridized together, producing a double stranded DNA fragment 12 which incorporates the recommended sequence changes to permit efficient expression of rBSt in E. coli., and has a codon for alanine inserted at the second position as shown by the underlined sequence. This DNA molecule also has the 5' complementary overhang for XbaI and the blunt end site for PvuII. The oligonucleotide is ligated into the isolated pUC8-BSt' vector, and transformed into competent E. coli. cells. Confirmation of the construction is obtained by sequencing the region. The new vector is designated pUCS-BSt'-ala.

Construction of the ala rBSt gene—pUC19(d)BSt-ala—Chart 8.

DNA of the transition vector pUC19(d)BSt (Chart 2) is digested with XbaI and PstI. The large vector fragment 13 (2.7 kb) is isolated. Next, pUCS-BSt'ala (Chart 7) is digested with XbaI and PstI restriction endonucleases and a 300 bp fragment 14 which encompasses the front half of the rBSt gene containing the ala codon insertion is isolated. The vector fragment of pUC19(d)-BSt and fragment 14 are ligated together and transformed into competent E. coli. cells. This resultant vector is designed pUC19(d)-BSt-ala and can be used as the transition vector for the position 98 base changes following the steps described in Example 2A above.

Example 3

A site-directed mutagenic technique for double-stranded primer extension is used to introduce altered codons for serine and proline at amino acid position 99 in the rBSt cDNA m4 gene (PCT patent application PCT/US 88/00328, filed 27 Jan. 1988 and incorporated herein by reference). In this method, the target sequence is cloned into a suitable plasmid and plasmid DNA is prepared. The plasmid DNA is denatured by treatment with sodium hydroxide which causes "nicks" in the DNA molecule deoxyribose-phosphate backbone. This relaxes the DNA and permits an oligomer containing the desired sequence changes to hybridize to the plasmid sequence containing the position 99 residue of BSt. The 3' end of the oligomer generates a primer for the DNA polymerase activity of the reverse transcriptase which extends the primer, synthesizes a new DNA strand containing the mutagenic oligomer and displaces the normal complementary strand. The extension reaction increases the probability of the incorporation of the oligomer-directed change. The DNA is transformed into competent cells and the resultant colonies are screened by colony filter hybridization. Plasmid DNA is isolated and sequenced from positive candidates.

The oligomers used to construct the position 99 serine and proline changes in the rBSt m4 gene are produced by techniques previously described (PCT/US 88/00328). An oligonucleotide so produced and designated CST-88 (Chart 9) contains the change on the DNA sequence asparagine AAC to serine TCT and another designated CST-89 (Chart 9) contains the asparagine AAC to proline CCG change. They are both designed with a Tm of 53° C. thus allowing for hybridization at 40° C. and stringent washing at 46° C. as set forth above.

In parallel experiments the serine and proline oligomers are hybridized to the pBR322 derived vector pTrp-BStm4. This vector contains the trp promoter and the m4 cDNA for rBSt (PCT/US 88/00328). After primer extension, the DNA is used to transform competent cells of MC1000 (available in the Experiments with Gene Fusion Strain Kit, Cold Spring Harbor Laboratory, Cold Spring Harbor, N.Y.). The transformed cells are plated to give 100–200 colonies on ten plates. The colonies are then transferred onto nitrocellulose. The cells are lysed and their DNA affixed to the filter. Radiolabeled oligomer probes are prepared from CST-88 and CST-89 by the oligomers with kinase and 32P-ATP. Details of the colony filter hybridization probing are set forth above.

Six candidates give a very strong positive signal on the autoradiogram for the serine mutagenesis. Plasmid DNA is isolated for each candidate and sequenced. One of the candidates is found to contain the serine change. The mutated gene contained therein is designated m4-99ser. For the proline mutagenesis, six positive candidates have been analyzed by DNA sequencing and two have been found to contain the desired change. These mutated genes are designated m4-99pro.

The m4-99ser and m4-99pro genes are excised from the parental vector as an EcoRI-HindIII fragment and cloned into the EcoRI-HindIII restriction sites of the pURA-m4 vector (PCT/US 88/00328). Chart 10 shows the cloning of the m4-99ser gene into the pURA-m4 vector. The identical construction is carried out for the m4-99pro gene. Upon sequence confirmation of the clonings, the vectors are designated pURA-99Ser and pURA-99Pro. These vectors are transformed into fermentation expression strain BST-1C (PCT/US 88/00328).

Transformed cells from each of the clonings are induced and samples analyzed by SDS-PAGE to assess the ability of the cells to express the modified rBSt genes under non-optimized conditions. Results of SDS-PAGE analysis showed that pURA-99Ser produced rBSt in three individual inductions at 13.8%, 14.6% and 26.4% of total cellular protein. Results of SDS-PAGE analysis showed pURA-99Pro in four separate inductions expressed rBSt at 28.2%, 29.6%, 34.0% and 41.9% of total cellular protein.

Because of poor mutagenic efficiency, the mutant oligomer must be constructed so that there is at least a 5° C. temperature difference between its Tm and that of the native sequence. Without this difference, effective screening of the candidates cannot be accomplished.

Example 4

Following the techniques of Example 3, but substituting the appropriate oligomers encoding the desired amino acids (C-ST 90 and C-ST 91, Chart 9), BSt analogs having aspartic acid and glutamic acid at position 99 have also been constructed.

Example 5

Analogs having two amino acids substituted in place of the position 99 asparagine (Ser-Ser and Ser-Asp) are constructed by following the site directed protocol of Kramer et al., Nucl. Acids Res., 12:9441–56 (1984) as described in the "Site Directed Mutagenesis Kit", commercially available from Boehringer Mannheim Biochemicals, PO Box 50816, Indianapolis, Ind. 46250 (see also, Kramer, W. and H-J Fritz, Meth. Enz., 154:350–67 (1987)). The procedure requires cloning the DNA sequence which is to be modified into the M13mp9 vector. This is done by digesting vector pURA-m4 (PCT/US 88/00328) with the restriction enzymes EcoRI and BamHI and isolating a DNA fragment approximately 870 bp in size. This fragment contains the E. coli tryptophan (trp) promoter, the trpL ribosome binding site and the entire BSt gene sequence. This fragment is cloned into the EcoRI and BamHI restriction sites of the M13mp9 vector using known techniques (Maniatis et al, Molecular Cloning: A Laboratory Manual, Cold Spring Harbor Publication, Cold Spring Harbor, N.Y.; J. Messing, Meth. Enzym., 101:20–98 (1983)). Single stranded DNA is isolated using the derived vector M13mp9-m4 (Messing, supra) and used in the mutagenesis procedure as previously described. Cloning of these analogs into the pURA expression vector is done as described in Example 3, in which the double-stranded DNA of the M13 vector, supra, is substituted for the pBR322 vector.

Example 6

A position 99 analog having glycine substituted for asparagine is also constructed using the techniques described in Example 3. The mutagenesis oligonucleotide used is designated CST84 (Chart 9) and encodes the change to glycine.

Example 7

Biological Assay.

Samples of rBSt and rBSt position 99 analogs are examined for relative potency using the hypophysectomized (pituitary surgically removed) rat growth bioassay. Two hundred hypophysectomized female Sprague Dawley rats weighing between 75 and 150 grams are used in each experiment. They are fed a pelleted rat food (Purina) and watered with deionized and rechlorinated water (ad libitum). Room conditions are set at a temperature of 80° F. and relative humidity of 50%. Air exchange is approximately 20 exchanges per hour and the photoperiod is set at 12 hours light and 12 hours dark, with the light cycle commencing at approximately 6:00 a.m.

The rats are monitored for a 12-day preliminary period to allow for adaptation to environmental and feeding conditions. Body weights are obtained on four occasions between days one and twelve. Rats which show weight losses of one gram per day or less or weight gains of 2 grams or less during the preliminary period are selected for injection with BSt. Only data from rats which are completely hypophysectomized as demonstrated by post mortem evaluation will be included in the final analysis. The rats are ranked according to ascending magnitude of average daily weight gain (ADG) and seven blocks of 25 rats are created. Treatments within each block are randomly assigned.

BSt treatments are begun and last 10 days. During this time, test compounds are injected twice daily for nine days and body weights are monitored using a top loading balance Mettler Model 3600 equipped with programming (lab-Pac) which determines the weight of the animals while taking into account their movements.

Stock solutions of rBSt at 2 mg/ml are prepared in a buffer of 0.03M sodium bicarbonate and 0.15M sodium chloride at pH 9.5. To facilitate suspension of rBSt, the lyophilized preparations are first dissolved in this buffer at pH 10.8, pH is then adjusted to 9.5 using 2N hydrogen chloride and brought to final volume using the stock buffer at pH 9.5 and filtered as necessary.

The stock solutions are diluted using stock buffer (pH 9.5) to solutions of 37.5, 75, 150 and 300 mg of protein/ml. The experimental rats are injected subcutaneously twice daily with 100 μl of the respective solutions and controls receive 100 μl of buffer. The experiment lasts 10 days with average daily weight gain monitored.

A statistical analysis of the relative potency for the various test samples of rBSt is as follows: native rBSt with asparagine at position 99 served as an analytical standard and is assigned relative potency value of 1.00. This sample has a potency of 1.15 relative to a sample of pituitary-derived bovine somatotropin. The rBSt analogs in which aspartic acid, glutamic acid, glycine, proline, serine, and serine-serine are substituted for the asparagine at position 99, has relative potencies (respectively) of 2.30, 3.00, 2.96, 2.50, 3.06, and 3.03 relative to rBSt control. These values are significant at the 95% confidence level.

Example 8

Activity of various position 99 analogs is demonstrated. The parameter measured is to estimate differences in 3.5% fat corrected milk yield (FCM) of lactating dairy cows injected intramuscularly with native rBSt, the glycine-99 (Gly-99) rBSt of Example 6, the serine-99 (Ser-99) rBSt of Example 3 and the aspartic acid-99 (Asp-99) rBSt of Example 4. Holstein cows (45) are ranked from high to low milk yield based on milk yield on days 3 and 2 prior to initiation of rBSt injections. The cows are assigned randomly in replicates, based upon milk yield, to 9 experimental groups: no injection (Control), 5 mg and 20 mg Gly-99 rBSt daily, 5 mg and 20 mg Ser-99 rBSt daily, 5 mg and 20 mg Asp-99 rBSt daily, and 5 mg and 20 mg native rBt daily. Cows are injected intramuscularly in the semitendinosus muscle once daily for 21 days. Twice daily milk weights are recorded for three days prior to initiation of injection, during the 21 days of injections, and for five days after the last injection. Concentration of rBSt is expected to be 10 mg/ml.

The concentration of residual post-injection rBSt solutions, measured by HPLC, averaged 11.5 for native rBSt, 12.1 for Asp-99 rBSt, 11.6 for Gly-99 rBSt, and 11.6 for Ser-99 rBSt. The area percent is greater than 99% normal rBSt for Gly-99 rBSt (by "normal rBSt" is meant the amino acid sequence encoded by a particular gene, i.e., no degradation products, etc.), for Ser-99 rBSt, and for Asp-99 rBSt, but averaged 90.5 normal rBSt for native rBSt. Native rBSt averaged 2% early-early eluting rBSt and 7.6% early eluting rBSt.

Statistical analyses of the FCM among experimental groups are based on average FCM for days 1 to 21 of injections using the three days prior to initiation of injections as the covariate. Average daily FCM (kg/day) is not statistically significantly different for either form of rBSt (P<0.12) or dose X form of rBSt interaction (P<0.90). However, since the statistical significance is P<0.12 for form of rBSt, an attempt is made to gain additional information on the relative potency among the forms of rBSt. Based on comparisons among the four forms of rBSt, there is a suggestion (P<0.05) that FCM of cows injected with Ser-99 rBSt is greater than FCM for cows injected with either Gly-99 rBSt or native rBSt. There is no suggestion of a difference in FCM of cows injected with Ser-99 rBSt compared to cows injected with Asp-99 rBSt or among cows injected with Gly-99 rBSt, Asp-99 rBSt, and native rBSt. FCM of cows administered 20 mg rBSt is statistically significantly greater than cows administered 5 mg.

| Experimental Group | Mean FCM Relative to Days of Injection | | | | Percentage Change for Days | |
|---|---|---|---|---|---|---|
| | 1–3 pre | 1–21 during | 1–5 post | Change[a] (kg/day) | 1–21 during[a] | 1–5 post[b] |
| Control | 27.6 | 26.1 | 26.1 | −1.5 | −5.4 | 0 |
| Native 5 mg | 28.2 | 28.0 | 26.8 | −0.2 | −0.7 | −4.3 |
| Native 20 mg | 26.6 | 30.2 | 26.0 | 3.6 | 13.5 | −13.5 |
| Asp-99 5 mg | 28.1 | 29.2 | 29.2 | 1.1 | 3.9 | 0 |
| Asp-99 20 mg | 24.5 | 29.0 | 27.0 | 4.5 | 18.4 | −6.9 |
| Gly-99 5 mg | 29.3 | 29.4 | 17.2 | 0.1 | 0.3 | −7.5 |
| Gly-99 20 mg | 26.4 | 29.8 | 28.6 | 3.4 | 12.9 | −4.2 |
| Ser-99 5 mg | 28.8 | 31.0 | 30.4 | 2.2 | 7.6 | −1.9 |
| Ser-99 20 mg | 28.9 | 33.5 | 31.6 | 4.6 | 15.9 | −5.7 |

[a]Days 1 to 21 of injection relative to days 1 to 3 pre-injection.
[b]Days 1 to 5 post-injection relative to days 1 to 21 of injection.

Example 9

Activity of other position 99 analogs is demonstrated in a separate study from that reported in Example 8. Again, the parameter measured is to estimate differences in 3.5% fat corrected milk yield (FCM) of lactating dairy cows injected intramuscularly with native rBSt (clinical rBSt) that has asparagine at position 99, rBSt with proline substituted for asparagine at position 99 (Pro-99 rBSt), and rBSt with glutamic acid substituted for asparagine at position 99 (Glu-99 rBSt). Holstein cows (35) are ranked from high to low milk yield based on milk yield on days 3 and 2 prior to initiation of rBSt injections. The cows are assigned randomly in replicates, based upon milk yield, to 7 experimental groups: no injection (Control), 5 mg and 15 mg Pro-99 rBSt daily, 5 mg and 15 mg Glu-99 rBSt daily, and 5 mg and 15 mg native rBSt daily. Cows are injected intramuscularly in the semitendinosus muscle once daily for 7 days. Twice daily milk weights are recorded for three days prior to initiation of injection, during the 7 days of injections, and for five days after the last injection.

The dose averaged 5.04 mg, 4.88 mg, and 5.03 mg for cows assigned to receive the 5 mg dose of Pro-99, Glu-99, and native rBSt respectively. Cows assigned to receive 15 mg rBSt received 15.12 mg, 14.64 mg, and 15.10 mg rBSt for cows of the Pro-99, Glu-99, and native rBSt respectively. The percentage of early-early eluting rBSt, early eluting rBSt, oxidized rBSt, and post-oxidized rBSt appeared to be similar for native rBSt, Glu-99 rBSt, and Pro-99 rBSt. Statistical analyses of the FCM among Experimental Groups are based upon average FCM for days 1 to 7 of injections using the three days prior to initiation of injections as the covariate. The FCM for cows of the native rBSt, Pro-99 rBSt, and Glu-99 rBSt groups is 28.7, 28.8, and 28.8 (P=0.95). Therefore, there is no suggestion of a difference of FCM for cows receiving native rBSt, cows receiving rBSt with glutamic acid substituted for asparagine at position 99, and cows receiving rBSt with proline substituted for asparagine at position 99. FCM is significantly greater for cows of the 15 mg rBSt group than for cows of the 5 mg rBSt group. Upon cessation of rBSt injections, FCM of rBSt previously injected cows decreased at similar rates during the 5 days after cessation of rBSt injections.

Example 10

To increase the growth rate in cows, young beef steers are selected for treatment. Recombinant deamidated bovine somatotropin is administered subcutaneously to each animal at a rate of 200 milligrams per day for 100 days. The animals are permitted to eat and drink at will.

Example 11

To increase the number of mammary parenchymal cells in dairy heifers, cows that are about 30 days before the expected onset of puberty are selected for treatment. Each animal receives recombinant deamidated bovine somatotropin administered subcutaneously at a rate of 200 milligrams per day for 100 days at which point the animals should be bred according to normal management practices. The animals are permitted to eat and drink at will.

Example 12

The aqueous stabilities of three of the rBSt position 99 analogs, having glycine, serine, and aspartic acid substituted for asparagine, are compared with that of native (asparagine at 99) rBSt under two sets of incubation conditions. The first set of incubations is carried out in 50 mM sodium carbonate, pH 10.0 at ambient temperature (protein concentration 20 mg/ml) to simulate conditions similar to those encountered during the isolation and formulation of rBSt. The second set of incubations is carried out in a pH 7.4 Ringer's solution at 37° C. (protein concentration 5 mg/ml) to simulate exposure to physiological conditions. All incubation samples are prepared aseptically. Samples are removed from the incubations over a three week period and stored at −20° C. prior to analysis by isoelectric focusing, SDS-PAGE, and reversed phase HPLC.

The glycine 99 and serine 99 rBSt analogs have IEF patterns that are virtually indistinguishable from native rBSt prior to incubation while the IEF pattern of native asparagine 99 rBSt is shifted approximately 1.2 pH units lower due to the introduction of the negative charge at position 99. The major difference noted between the IEF patterns of incubated samples of native rBSt and the position 99 analogs is the rate at which more acidic rBSt species are formed. The IEF pattern of native rBSt degraded into more acidic rBSt species at a faster rate under both sets of incubation conditions than did the IEF patterns of the position 99 analogs. One additional difference between the IEF patterns of native rBSt and the analogs is the presence in incubated native rBSt samples of IEF bands that have been associated with a chain cleavage between residues 99 and 100 of the rBSt molecule. These bands are not observed in the IEF patterns of the position 99 analogs.

When analyzed under non-reducing conditions, the SDS-PAGE behavior of incubated samples of the position 99 analogs is identical to that of native rBSt. When examined under reducing conditions, however, the major rBSt fragment formed during the incubation of native rBSt is found to be absent in the position 99 analogs. Replacement of the asparagine residue at position 99 with either glycine, serine, or aspartic acid therefore eliminated the peptide bond cleavage between residues 99 and 100. The two peptides formed as a result of this cleavage in native rBSt are normally held covalently intact by the disulfide bond between cysteine residues 53 and 164, thus the difference between the reduced and non-reduced samples.

Reversed phase HPLC is used to measure the amount of isoaspartate formation and chain cleavage which occurred at position 99 of the rBSt molecule since these species elute earlier upon reversed phase HPLC than native rBSt. rBSt which contained a chain cleavage between positions 99 and 100 of the rBSt molecule accounted for 8.5 area percent of native rBSt at the conclusion of the pH 10.0 incubation, and for 11.1 area percent of native rBSt at the conclusion of the pH 7.4 incubation. By comparison, the amount of the rBSt analogs which eluted in this position is less than 0.5 area percent. rBSt which eluted in the position of isoaspartic acid 99 rBSt accounted for 35.8 area percent of native rBSt at the conclusion of the pH 10.0 incubation, and for 49.9 area percent of native rBSt at the conclusion of the pH 7.4 incubation. Of the position 99 rBSt analogs, aspartic acid 99 rBSt showed the greatest formation of rBSt which eluted in this position: 3.8 area percent at the conclusion of the pH 10.0 incubation and 13.9 area percent at the conclusion of the pH 7.4 incubation.

Therefore, the position 99 analogs of the instant invention show superior aqueous stability relative to native asparagine 99 rBSt.

Example 13

Following the teachings of the preceding examples with appropriate modifications, similar analogs to porcine, human, ovine, horse, rat, monkey and avian somatotropins may also be produced by replacing the asparagine residues at position 99 (S. S. Abdel-Meguid, et al., Proc. Natl. Acad. Sci. USA, 84:6434–37 (1987). Because of the close sequence homology between mammalian somatotropins in this region of the molecule, the asparagine residue corresponding to BSt asparagine 99 is likely the third residue in a β-turn in each of these other somatotropins thus leading to isoaspartic acid formation and chain cleavage as with BSt. If this is found to be the case for other somatotropins by analysis of the products as set forth above, substituting an appropriate amino acid for the asparagine 99 would obviate the isoaspartate formation and chain cleavage.

CHART A.
Amino Acid Sequence of Bovine Somatotropin 1
ala phe pro ala met ser leu ser gly leu phe ala asn ala val 20
leu arg ala gln his leu his gln leu ala ala asp thr phe lys 40
glu phe glu arg thr tyr ile pro glu gly gln arg tyr ser ile 60
gln asn thr gln val ala phe cys phe ser glu thr ile pro ala pro thr gly lys asn glu ala gln gln lys ser asp leu glu leu 80
leu arg ile ser leu leu leu ile gln ser trp leu gly pro leu 100
gln phe leu ser arg val phe thr asn ser leu val phe gly thr 120
ser asp arg val tyr glu lys leu lys asp leu glu glu gly ile leu ala leu met arg glu leu glu asp gly thr pro arg ala gly 140
gln ile leu lys gln thr tyr asp lys phe asp thr asn met arg 160
ser asp asp ala leu leu lys asn tyr gly leu leu ser cys phe 180
arg lys asp leu his lys thr glu thr tyr leu arg val met lys 190
cys arg arg phe gly glu ala ser cys ala phe

CHART B
Original Sequence of Bovine Somatotropin

```
                                 98
5' CTG.CAG.TTC.CTC.AGC.AGA.GTC.TTC.ACC.AAC.AGC.TTG.GTG 3'
                                 ---
                                 asn
```

Synthetic Oligonucleotides

```
                                 98
5' CTG.CAG.TTC.CTC.AGC.AGA.GTC.TTC.ACC.GAC.AGC.TTG.GTG 3'
                                 ---
                                 asp 5' CTG.CAG.TTC.CTC.AGC.AGA.GTC.TTC.ACC.GAA.AGC.TTG.GTG 3'
                                 ---
                                 glu
```

CHART 1
Construction of pUC19(d)

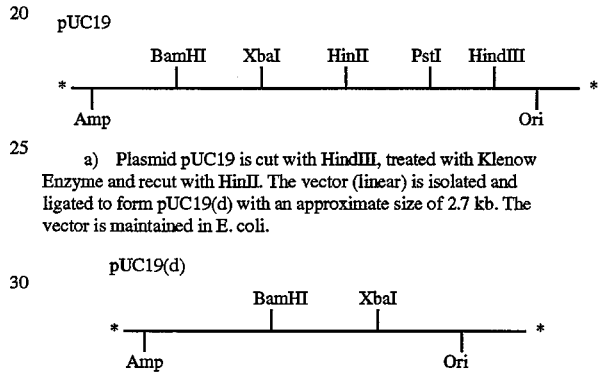

a) Plasmid pUC19 is cut with HindIII, treated with Klenow Enzyme and recut with HinII. The vector (linear) is isolated and ligated to form pUC19(d) with an approximate size of 2.7 kb. The vector is maintained in E. coli.

Key

Amp = Ampicillin resistance.
Ori = Origin of replication.

CHART 2.
Construction of pUC19(d)-bSt a) Plasmid pBGH 33-4 (5.2 (kb) is cut with XbaI and BamHI to isolate the intact BGH gene (0.9 kb).

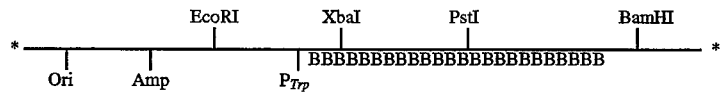

Fragment 1

b) Plasmid pUC19(d) from Chart 1 is cut with XbaI and BamHI to yield fragment 2 (2.7 kb).

Fragment 2

c) Fragments 1 and 2 are isolated and ligated using T4 DNA ligase to yield plasmid pUC19(d)-bSt.

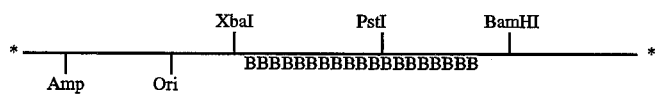

-continued
CHART 2.
Construction of pUC19(d)-bSt

Key

Amp = Ampicillin resistance.
Ori = Origin of replication.
P_Trp = Tryptophan promoter.
B = rbSt cDNA.

CHART 3.
Construction of pM13-BSt' a) Plasmid pBGH 33-4 is cut with PstI and BamHI and fragment 3 (700 kb) containing the 3' end of the BSt gene is isolated.

Fragment 3

b) Plasmid pM13 mp-19 RF (7.25 kb) is cut iwth PstI and BamHI and fragment 4 (7.20 kb) is isolated.

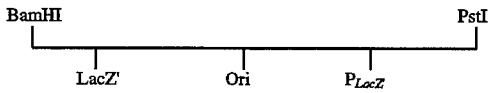

-continued
CHART 3.
Construction of pM13-BSt' c) Fragments 3 and 4 are ligated to yield pM13-BSt.

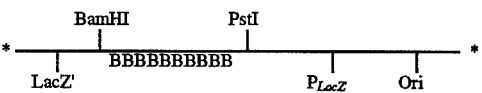

Key

B = Bovine somatotropin.
LacZ' = α fragment of β-galactosidase.
P_LacZ = Promoter for fragment of β-galactosidase.
Ori = Origin of replication.

CHART 4.
Construction of pUC19(d)-bSt* a) Single stranded DNA from M13-bSt grown in dam⁻ cells are hybridized with a synthetic oligonucleotide having an appropriate base change at the codon coding for asparagine 98 to insert aspartic acid.

```
                                               Δ
5'*  GAC GTC AAG GAG TCG TCT CAG AAG TGG GTG TCG AAC CAC  *3'
...  CTG CAG TTC CTC AGC AGA GTC TTC ACC AAC AGC TTG GTG...
``` b) The primer is extended beyond the BamHI site of the rbSt 3' end using PolK (Klenow fragment). The heteroduplex portion of the vector is excised using PstI and BamHI and isolated to yield fragment 5.

c) pUC19(d)bSt (Chart 2) is cut with PstI and BamHI to remove the 3' portion of the bSt cDNA. Fragment 6 (3.0 kb) containing the vector portion of pUC19 and the 5' portion of bSt is isolated.

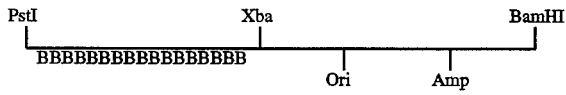

d) Fragments 5 and 6 are ligated and the resulting heteroduplex is transformed into E. coli which forms two populations of homoduplexes. The homoduplex containing the appropriate modification at position 98 (aspartic acid) is selected by gel sequencing and isolated for expression. The vector is designated as pUC19(d)-bSt*.

```
          XbaI       PstI     BamHI
  5'*──────┼──────────┼────────┼─────────────────────── *3'
           BBBBBBBBBBBBBBBBB
                     Δ          Amp    Ori
```

-continued
CHART 4.
Construction of pUC19(d)-bSt*

Key

B = rbSt cDNA.
Δ = Site of nucleotide change.
Amp = Ampicillin resistance.
Ori = Origin of replication.

CHART 5.
Construction of pBGH33-4-"Glu98"

a) Plasmid pUC19(d)-bSt* is cut with XbaI and BamHI to yield fragment 7 (1.0 kb) which contains the entire coding sequence for rbSt as modified at position 98.

Fragment 7

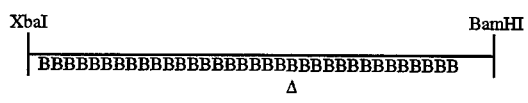

b) Expression vector pBGH33-4 is cut with BamHI and fragment 8 (4.8 kb) is isolated.

Fragment 8

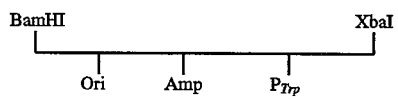

c) Fragments 7 and 8 are ligated to form the expression vector pBGH33-4-"Glu98" (5.8 kb).

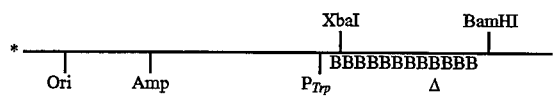

Key

Ori = Origin of replication.
Amp = Ampicillin resistance.
P_Trp = Tryptophan promoter.
B = rbSt cDNA.
Δ = Site of nucleotide change.

CHART 6.
pUC8-bSt' a) Plasmid pBGH33-4 (Chart 2) is cut with EcoRI and PstI to obtain fragment 9 (550 bp) which is isolated by gel electrophoresis and electroelution.

Fragment 9

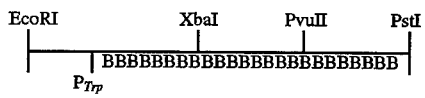

b) Plasmid pUC-8 is cut with EcoRI and PstI to obtain fragment 10 (2.7 kb) which is isolated by gel electrophoresis and electroelution.

-continued
CHART 6.
pUC8-bSt'

Fragment 10

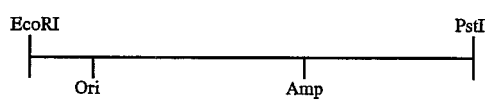

c) Fragments 9 and 10 are ligated to yield pUC8-bSt' (3.3 kb).

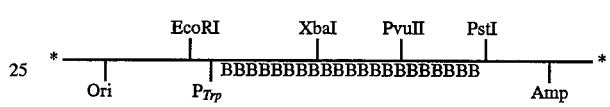

Key

Amp = Ampicillin resistance.
Ori = Origin of replication.
P_Trp = Tryptophan promoter.
B = rbSt cDNA.

CHART 7.
The Construction of pUC-bSt'ala.

a) Plasmid pUC8-bSt' (Chart 6) is cut with XbaI and PvuII to yield fragment 11 which is purified by gel electrophoresis and isolated by electroelution.

Fragment 11

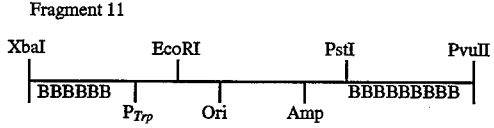

b) Fragment 12 (72 bp), a double stranded oligonucleotide containing the 5' portion of bSt and incorporating an alanine codon at position one, is artificially synthesized.

Fragment 12

c) Fragments 11 and 12 are ligated with t4 ligase to yield pUC8-bSt'ala.

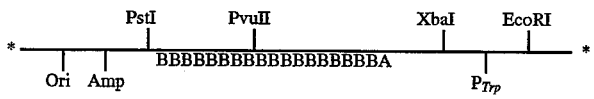

Key
Amp = Ampicillin resistance.
Ori = Origin of replication.
B = Bovine somatotropin cDNA.
A = Alanine codon.
P_Trp = Tryptophan promoter.

CHART 8.
Construction of pUC19(d)bSt-ala a) Plasmid pUC19(d)bSt (Chart 2) is cut with XbaI and PstI and fragment 13 (2.7 kb) is gel isolated.

Fragment 13

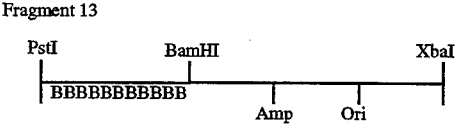

b) Plasmid pUC8-bSt'ala (Chart 7) is cut with XbaI and PstI to yield fragment 14 (300 bp) which is gel isolated.

Fragment 14

c) Fragments 13 and 14 are ligated to yield pUC19(d)bSt'ala (3.3 kb).

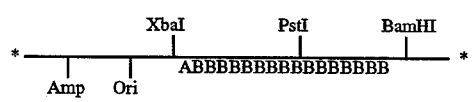

Key

Amp = Ampicillin Resistance.
Ori = Origin of replication.
B = Bovine somatotropin cDNA.
A = Alanine codon.

CHART 10.
Cloning of the m4-99ser gene into the pURA Vector

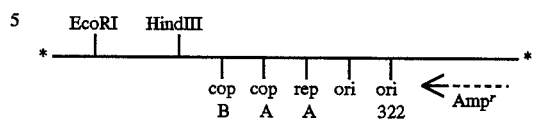

Fragment 2

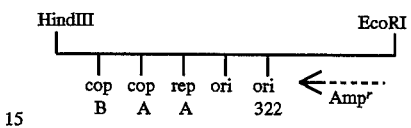

3) Fragments 1 and 2 are then ligated together to produce plasmid pURA-99ser.

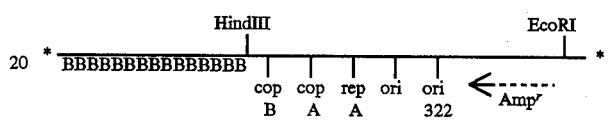

B = bSt m4-99ser gene

We claim:

1. A non-naturally occurring mammalian somatotropin in which the amino acid corresponding to asparagine at position 99 of a native somatotropin is replaced with a different amino acid selected from the group consisting of aspartic acid and glutamic acid.

CHART 9.
Oligonucleotides Used for Constructing rBSt Analogs

| | |
|---|---|
| C-ST 84 (gly) | 5'-GTCTTCACCGGTAGCTTGGTG |
| C-ST 88 (ser) | 5'-GTCTTCACCTCTAGCTTGGTG |
| C-ST 89 (pro) | 5'-GTCTTCACCCCGAGCTTGGTG |
| C-ST 90 (asp) | 5'-GAGTCTTCACTGATAGCTTGGTG |
| C-ST 91 (glu) | 5'-GAGTCTTCACTGAAAGCTTGGTG |
| JM 23 (ser—ser) | 5'-AGCAGAGTCTTCACCTCTTCCTCTTTGGTGTTTGGCACC |
| JM 57 (ser—asp) | 5'-TCAGCAGAGTCTTCACCTCTGACTCCTTGGTGTTTGGCACCTCGG |

2. A somatotropin according to claim 1 wherein the asparagine is replaced with aspartic acid.

3. A somatotropin according to claim 1 wherein the asparagine is replaced with glutamic acid.

4. A somatotropin according to claim 1 which is bovine somatotropin.

5. A somatotropin according to claim 2 which is bovine somatotropin.

CHART 10.
Cloning of the m4-99ser gene into the pURA Vector

1) A plasmid containing the m4-99ser gene is digested with EcoRI and HindIII to produce Fragment 1.

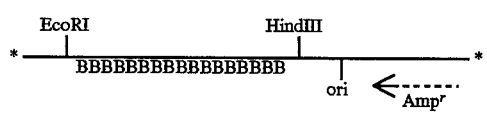

Fragment 1

2) Plasmid pURA-m4 is digested with EcoRI and HindIII to produce Fragment 2.

6. A somatotropin according to claim 3 which is bovine somatotropin.

7. A somatotropin according to claim 1 which is porcine somatotropin.

8. A method for enhancing the growth of an animal which comprises administering to the animal an effective amount of a somatotropin of claim 1 which is bioactive in the animal.

9. The method of claim 8 wherein the animal is a bovine.

10. The method of claim 8 wherein the animal is a porcine.

11. A method for increasing milk production in a cow comprising administering to the cow an effective amount of a bovine somatotropin of claim 1.

* * * * *